United States Patent [19]

Mruk et al.

[11] 4,396,486

[45] Aug. 2, 1983

[54] ION SELECTIVE ELECTRODE ELEMENT

[75] Inventors: Norbert J. Mruk, Williamsville; Robert A. Falls, Orchard Park, both of N.Y.

[73] Assignee: Graphic Controls Corporation, New York, N.Y.

[21] Appl. No.: 410,699

[22] Filed: Aug. 23, 1982

[51] Int. Cl.$^3$ .................... G01N 27/26; G01N 27/30; G01N 27/46
[52] U.S. Cl. .................................................. 204/419
[58] Field of Search ............................... 204/419, 1 T

[56] References Cited

U.S. PATENT DOCUMENTS

| 3,563,874 | 2/1971 | Ross et al. ............................ 204/419 |
| 3,591,464 | 7/1971 | Frant et al. .......................... 204/1 T |
| 3,766,022 | 10/1973 | Higashiyama et al. ............. 204/1 T |
| 3,796,642 | 3/1974 | Higashiyama et al. ......... 204/419 X |
| 3,798,147 | 3/1974 | Higashiyama et al. ............. 204/419 |
| 3,892,833 | 7/1975 | Hattori et al. .................. 204/1 T X |

*Primary Examiner*—G. L. Kaplan
*Assistant Examiner*—Nam X. Nguyen
*Attorney, Agent, or Firm*—Michael G. Berkman

[57] ABSTRACT

An ion selective potentiometric electrode component consisting essentially of a solid, plate-like interface element prepared by simultaneously co-precipitating $Ag_2S$, $Ag_2Se$, CdS and CdSe followed by compressing the precipitated material at an elevated temperature to provide a substantially impervious agglomerate having an X-ray diffraction pattern distinct from a composite pattern of the individual four components and characterized by improved response properties and enhanced sensitivity to cadmium ion concentration in solution.

6 Claims, 5 Drawing Figures

4,396,486

ION SELECTIVE ELECTRODE ELEMENT

BACKGROUND OF THE INVENTION

The present invention relates to an improved physical component for an ion-selective potentiometric electrode. More particularly, the invention is directed to a solid state interface plate or membrane providing greater ion definitiveness, improved ion sensitivity, and enhanced operational characteristics in the detection and quantitative determination of specific ions in solution.

Potentiometric techniques utilizing ion-selective electrodes for qualitative detection and for quantitative measurement of specific ions in solution have in recent years replaced other analytical methods including colorimetric, spectrographic and reagent-based procedures. Extensive developmental research time and funds have been directed toward improving the sensitivity, the specificity, and the response characteristics of ion-selective electrodes. A significant part of this work has dealt with improvements in solid state membrane compositions. Notwithstanding a substantial expenditure of investigative resources and the discovery of relevant parameters, much fundamental knowledge remains to be gleaned.

SUMMARY OF THE INVENTION

The present invention provides an improved interface plate or membrane for an ion-selective potentiometric electrode, characterized by enhanced ion sensitivity and superior quantitative response characteristics.

A principal aim of the invention is to provide a membrane element for use in an ion-selective electrode to facilitate qualitative detection of and quantitative measurement of specific ions in solution.

In a preferred embodiment of the invention, the membrane constitutes a sintered-like mass of particles formed as a disc-like element or plate sensitive to and responsive to cadmium ions in solutions.

An important feature of the invention is an enhanced ion sensitivity and a successful realization of an increased incremental voltage change as a function of ion concentration, all derived from a utilization of the improved solid state membrane of the invention.

A related feature of the invention is that ion-selective electrodes incorporating the membrane of the invention exhibit essentially linearly proportional voltage response curves over at least an eight-fold logarithmic cadmium concentration range including over a range of from about 0.1 molar to about $10^{-8}$ molar.

Yet another feature of the invention is the ease with which the improved compositions are prepared and processed for use.

An important facet of the invention is the discovery that a close structural relationship between different component salts may contribute to the establishment of a crystalline structure responsible for the enhanced efficacy of the solid membrane of the invention in analytical procedures.

Related important properties of the solid membrane of the invention are believed to be attributable to the formation of solid solutions of salts of elements to be detected, for example, cadmium.

Still another feature of the composite four-component co-precipitate of the invention as transformed into a unitary solid membrane through application of pressure and heat, is that an X-ray diffraction spectrum gives no lines characteristic of any of the four pure components, indicating the composite is a substitutional solid solution and not a mixture.

It is a feature of the four-component solid solution of the ion-selective electrode element of the invention that the X-ray diffraction pattern is also different from that of a pattern derived from a mixture of a co-precipitate of $Ag_2S$ and $Ag_2Se$ with a co-precipitate of $CdS$ and $CdSe$.

DETAILED DESCRIPTION OF THE PREFERRED EMBODIMENT

The preferred embodiment of the present invention is a four-component equi-molar co-precipitate of $Ag_2S$, $Ag_2Se$, $CdS$ and $CdSe$ prepared in accordance with the procedure set forth below:

Preparation of $Ag_2S/Ag_2Se/CdS/CdSe$ Coprecipitate

Silver nitrate (10.85 g.) and cadmium nitrate (10.32 g.) were dissolved in 1,000 ml. of deoxygenated, deionized water, which was previously acidified with 5 ml. of glacial acetic acid. Sodium sulfide nonahydrate (7.36 g.) and sodium selenide (4.00 g.) were dissolved in 1,000 ml. of deoxygenated, deionized water. Nitrogen was bubbled through this solution while the two ingredients were being dissolved. The mixed nitrate solution was slowly poured into the sulfide/selenide solution with vigorous stirring. The resulting dense black co-precipitate was allowed to settle and the mother liquor was decanted. The co-precipitate was washed ten consecutive times at room temperature with one liter portions of deionized water and twice with one liter portions of isopropanol at 60° C. Each wash consisted of stirring for 15–20 minutes followed by settling and decantation of the supernatant. The product was collected by suction filtration of a sintered glass filter funnel and dried at 100° C. for eight hours to yield 13.3 g. (99%) of co-precipitate. (Co-precipitate A)

Figure 3:
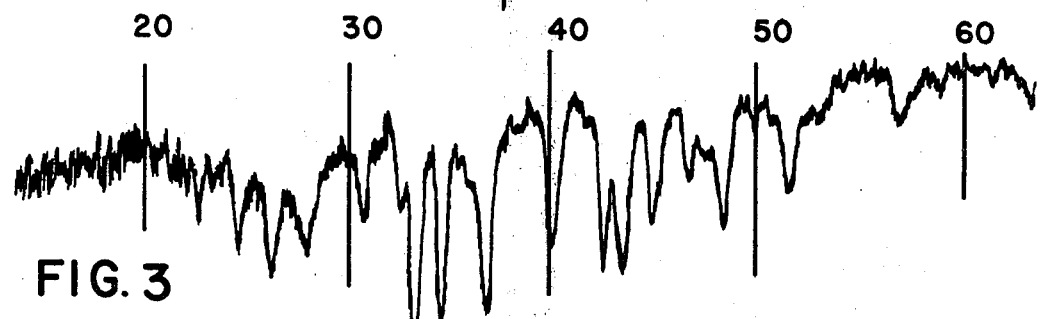
FIG. 3 is a print of the X-ray diffraction spectrum of a four-component pressed pellet of an equal-molar co-precipitate of $Ag_2S$, $Ag_2Se$, $CdS$ and $CdSe$.
Figure 4:
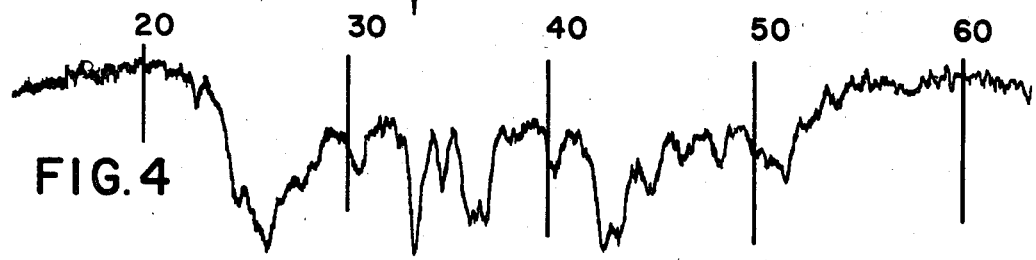
FIG. 4 is a print of the X-ray diffraction spectrum of a pressed pellet of a mixture of a co-precipitate of $Ag_2S$ and $Ag_2Se$ with a co-precipitate of $CdS$ with $CdSe$.

In fabricating the solid state pellet or membrane of the invention the above-described co-precipitate was compressed at an elevated temperature. Typical conditions imposed were pressure of 100,000 psi for one hour at about 350° F. The product, in the form of an ion-selective electrode pellet was subjected to x-ray diffraction examination using a General Electric X-ray Diffraction Spectrometer, employing K radiation ($\lambda = 1,50405$ A). A typical spectrum is shown in FIG. 3.

In order further to explore the nature of the novel four-component precipitate of the invention, a product was made by co-precipitating $Ag_2S$ with $Ag_2Se$, mixing the product with a co-precipitate of CdS with CdSe and transforming the mixture into a solid state pellet. The detailed laboratory procedures for preparing each co-precipitate are set forth below.

Preparation of $Ag_2S/Ag_2Se$ Co-Precipitate

Silver nitrate (20.69 g.) was dissolved in 1,000 ml. of deoxygenated, deionized water, which was previously acidified with 5 ml. of glacial acetic acid. Sodium sulfide nonahydrate (7.35 g.) and sodium selenide (4.00 g.) were dissolved in 1,000 ml. of deoxygenated, deionized water.

Nitrogen was bubbled through this solution while the two ingredients were being dissolved. The sulfide/selenide solution was slowly added to the silver nitrate solution with vigorous stirring. The co-precipitate was allowed to settle and the mother liquor was decanted. The co-precipitate was washed ten consecutive times at room temperature with one liter portions of deionized water and twice with one liter portions of isopropanol at 60° C. Each wash consisted of stirring for 15–20 minutes followed by settling and decantation of the supernatant. The product was collected by suction filtration on a sintered glass filter funnel and dried at 100° C. for eight hours to yield 16.5 g. (99.8%) of co-precipitate.

Preparation of CdS/CdSe Co-Precipitate

Cadmium nitrate (23.52 g.) was dissolved in 1,000 ml. of deoxygenated, deionized water which were previously acidified with 5 ml. of glacial acetic acid. Sodium sulfide nonahydrate (9.23 g.) and sodium selenide (5.00 g.) was dissolved in 1,000 ml. of deoxygenated, deionized water. Nitrogen was bubbled through this solution while the two ingredients were being dissolved. The cadmium nitrate solution was slowly poured into the sulfide/selenide solution with vigorous stirring. The resulting reddish-orange curdy precipitate settled very slowly. After the mother liquor was decanted, the co-precipitate was washed ten consecutive times at room temperature with one liter portions of deionized water and twice with one liter portions of isopropanol at 60° C. Each wash consisted of stirring for 5–10 minutes followed by settling and decantation of the supernatant. The product was collected by suction filtration on a sintered glass filter funnel and dried at 100° C. for eight hours to yield 11.81 g. (92%) of co-precipitate.

Equimolar $Ag_2S/Ag_2Se$ and CdS/CdSe co-precipitates were physically mixed together with a mortar and pestle in quantities which yielded a composition (Composition B) possessing equimolar concentrations of $Ag_2S$, $Ag_2Se$, CdS, and CdSe as found in Coppt. A. Composition B was also pressed into an electrode pellet under the same conditions as those used in the case of Coppt. A, and the pellet was assembled into a conventional ion selective electrode.

Figure 5:
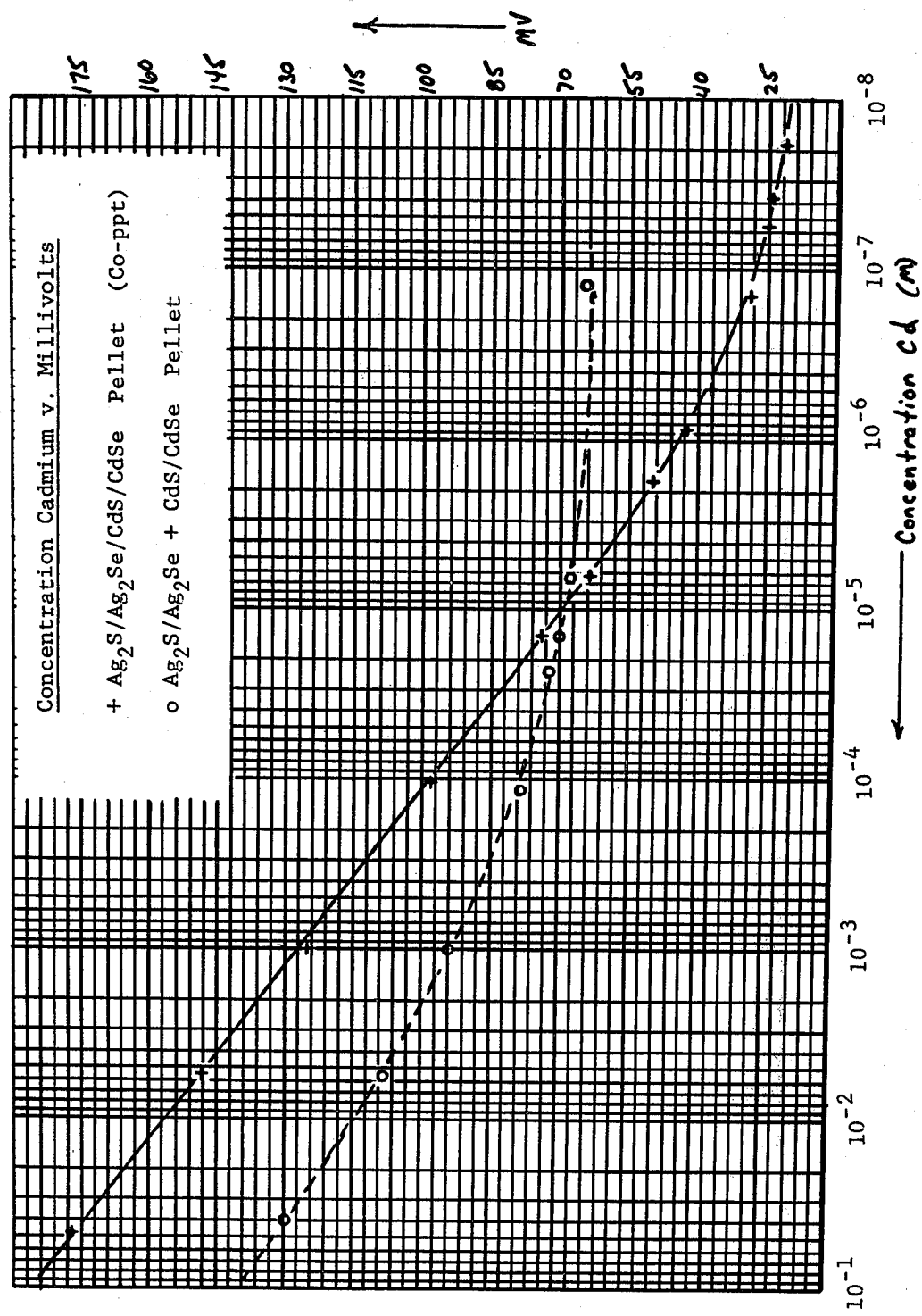
FIG. 5 is a graphic representation, on a semi-log coordinate scale, of the ion detection characteristics including voltage readings as a function of $Cd^{++}$ ion concentration for the four-component co-precipitate of the invention, and depicting similar data for a mixture of a co-precipitate of $Ag_2S$ and $Ag_2Se$ with a co-precipitate of $CdS$ with $CdSe$.

Evaluation of the two electrodes as cadmium ion selective electrodes yielded the following results (also see FIG. 5).

|  | Coppt. A | Composition B |
| --- | --- | --- |
| Limit of Detection ($Cd^{++}$) | $2 \times 10^{-7}$ | $5 \times 10^{-5}$ |
| Slope (mV per decade) | 29.2 | 18.7 |

The results and the attached graphical data clearly indicate the superiority of Coppt. A over Composition B. The electrode prepared from Coppt. A possesses a limit of detection which is 250 times lower than that of the electrode prepared from Composition B. Furthermore, the slope of the response line for the electrode of Coppt. A is essentially equal to the theoretical slope expected (29.6 mV) whereas that determined for the electrode of Composition B is significantly reduced, indicating a poorer response to cadmium ion.

The co-precipitate of the four-component combination silver and cadmium, sulfide and selenide of the invention shows structural differences from both the pure individual substances or from dual co-precipitates that are physically mixed. These data demonstrate a re-ordering of the crystalline matrix, of the four component co-precipitate showing a structural pattern incorporating each component into a new structure not akin to physical mixtures or combinations of co-precipitates and physical mixtures.

Figure 1:
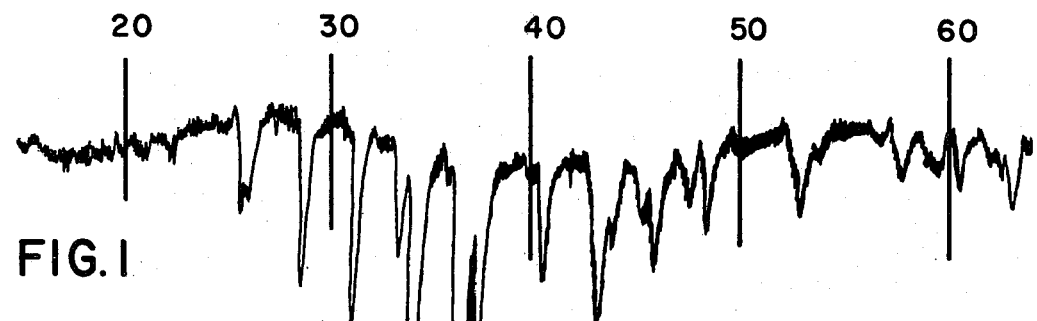
FIG. 1 is a print of the X-ray diffraction spectrum of $Ag_2S$.
Figure 2:
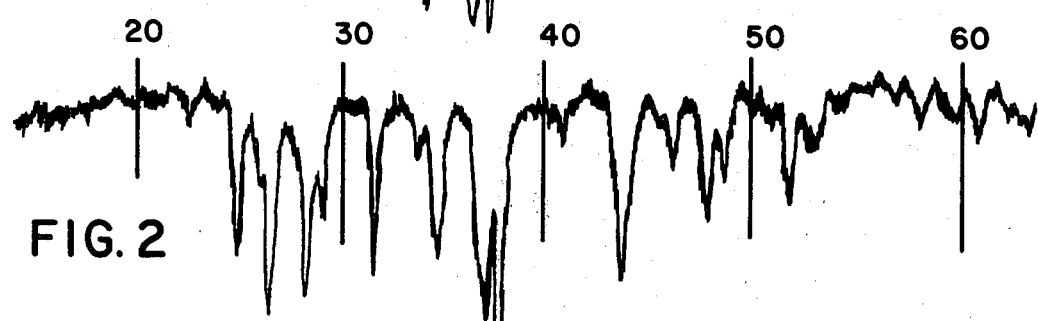
FIG. 2 is a print of the X-ray diffraction spectrum of a pressed pellet composed of a mixture of $CdS$ and $Ag_2S$.

That is, the four-component co-precipitates produce crystalline patterns unlike those of physical mixtures even if parts of the physical mixture are individual co-precipitates. That the structures produced by the co-precipitates are different is shown by different X-ray diffraction patterns (See FIGS. 2 and 3). A new chemical/physical material is clearly indicated.

The X-ray diffraction pattern of the four component co-precipitate of the present invention is markedly different from that of the physical mix of the $Ag_2S/Ag_2Se$ and CdS/CdSe co-precipitates, indicating that the four component co-precipitate possesses a crystalline structure different from either of the two individual solid solutions. Since the X-ray diffraction spectrum of the four component co-precipitate also differs from either the sum of the individual ingredients or the sum of the two Ag and Cd solid solutions, one can conclude that a new four-component solid solution is formed in the co-precipitate process. Comparison of the electrodes prepared from the mixture of the Ag and Cd solid solutions shows that this four-component solid solution possesses a new and unique crystalline structure which imparts cadmium sensing potentiometric properties that are superior.

What is claimed is:

1. A solid membrane for use as a component of an ion-selective potentiometric electrode,
    said membrane being sensitive to selective ions to facilitate a determination of the concentration thereof in solution,
    said membrane comprising pressed and intimately bonded particles derived from four-component co-precipitate of $Ag_2S$, $Ag_2Se$, CdS and CdSe, and
    said membrane being characterized in having a crystalline structure distinct from that derived from intermixing the individual compounds $Ag_2S$, $Ag_2Se$, CdS and CdSe and also distinct from that derived from intermixing a co-precipitate of $Ag_2S$ and $Ag_2Se$ with a co-precipitate of CdS and CdSe.

2. The composition as set forth in claim 1 wherein said four-component co-precipitate includes four components present in essentially equal molar concentrations.

3. The composition as set forth in claim 1 wherein said four-component co-precipitate comprises a unitary pellet-like aggregate of particles compressed at a pressure of about 100,000 psi and at a temperature of about 350° F.

4. The structure as set forth in claim 1 wherein an ion selective electrode incorporating said membrane exhibits an essentially logarithmically linear proportional voltage response curve over at least an eight-fold cadmium ion concentrational range including over a range of from about 0.1 molar to about $10^{-8}$ molar.

5. The structure as set forth in claim 1 wherein disposition of said membrane as an interface medium between a reference solution containing a fixed concentration of $Cd^{++}$ ion and exhibiting a fixed constant potential and a sample solution containing $Cd^{++}$ ion in solution and in a concentrational range of from about 0.1 molar to about $10^{-8}$ molar will effect production of a potential in the range of about 200 mv.

6. The method of producing an interface element for use in an ion-selective potentiometric electrode, said method comprising the steps of:

dissolving silver nitrate and cadmium nitrate in water in a ratio to provide a first solution containing two moles of silver ion for each mole of cadmium ion, dissolving sodium sulfide, and sodium selenide in water to provide a second solution having equimolar concentrations of sulfide ion and selenide ion, the molar concentrations of sulfide ion and of selenide ion being equal to the molar concentration of cadmium ion present in said first solution, blending said first solution and said second solution to produce an equi-molar co-precipitate of $Ag_2S$, $Ag_2Se$, CdS and CdSe, isolating said co-precipitate, and subjecting said co-precipitate to heat and to compression to form a unitary pellet-like element characterized by improved response properties and to cadmium ion concentration in solution.

* * * * *